United States Patent [19]

Portnoff

[11] 4,093,733

[45] June 6, 1978

[54] PARENTERAL SUSPENSIONS

[75] Inventor: Joel B. Portnoff, Philadelphia, Pa.

[73] Assignee: Merck & Co., Inc., Rahway, N.J.

[21] Appl. No.: 721,921

[22] Filed: Sep. 9, 1976

[51] Int. Cl.² .............................................. A61K 31/40
[52] U.S. Cl. .................................................... 424/274
[58] Field of Search ........................................ 424/274

[56] References Cited

PUBLICATIONS

Chem. Abst.-8th Collect. Index Subjects Indene-p. 15860s vol. 70-60821y (1969), & vol. 71-42339p (1969). MSD Price List No. 69: "Pharmaceuticals/Biologicals," Apr. 15, 1976, pp. 7, 10 & 21.

*Primary Examiner*—Stanley J. Friedman
*Attorney, Agent, or Firm*—Mario A. Monaco; Raymond M. Speer

[57] ABSTRACT

Improved anti-inflammatory suspensions for parenteral applications, comprising 1-(p-chlorobenzoyl)-2-methyl-5-methoxy-3-indolyl acetic acid as active ingredient.

2 Claims, No Drawings

PARENTERAL SUSPENSIONS

BACKGROUND OF THE INVENTION

The present invention is concerned with improved parenteral suspensions. As used herein, the term "parenteral" refers to introduction of the medicament suspension into the body of a patient otherwise than by way of the intestines. Specifically, the term refers to injection of the medicament suspension into the body. Since the medicament suspension cannot be injected intravenously, intramuscular injection is intended usually, although other injection sites or modes which are not intravenous may be employed.

Many useful anti-inflammatory compounds are solids. Those solids which are soluble in parenteral carriers or vehicles present little or no difficulty when preparing a formulation for parenteral use. However, those solids which are insoluble in parenteral carriers must be formulated as suspensions in order to obtain a proper delivery system. Moreover, forms of useful anti-inflammatory compounds which are insoluble in parenteral carriers are often found desirable in order to prolong the particular therapeutic action of the compound. Consequently, providing acceptable suspensions of useful anti-inflammatory compounds for parenteral use is a goal of pharmaceutical formulation.

An acceptable parenteral suspension possesses certain essential characteristics, among which are: that the suspended material should not settle too rapidly from the carrier to be available in the required concentration in the carrier for effective administration to the patient; that the particles of suspended material which do finally settle to the bottom of the vessel holding the suspension must not form an intractable hard cake but should be readily redispersed into a uniform suspension when the vessel is shaken; and that the total suspension must not be too viscous for efficient administration to the patient, but should pour freely.

Suspensions are prepared by use of either, vehicles structured to maintain discrete particles more or less permanently in suspension, without agglomeration or flocculation, or by the application of known principles of formulation chemistry to produce vehicles which permit flocs to form and settle, but which they are easily resuspended with slight agitation and remain uniformly dispersed or suspended during the period required for therapeutic administration. In this latter approach, flocculating agents are used in preparing the vehicle or carrier. However, depending upon the type of medicinal product employed, particular ratios of medicament, carrier and flocculating agent must be employed. These critical ratios cannot be determined beforehand and with some medicaments are extremely difficult to obtain at all.

There is a known anti-inflammatory agent useful in therapeutic treatment of inflammatory diseases; namely, 1-(p-chlorobenzoyl)-2-methyl-5-methoxy-3-indolyl acetic acid, which is insoluble in conventional parenteral carriers and consequently must be employed in the form of suspensions. However, use of this medicament has been impeded by the fact that it does not readily form acceptable suspensions in vehicles containing flocculating agents in the proportions normally employed in parenteral suspensions.

SUMMARY OF THE INVENTION

It has been found that, in accordance with the present invention, acceptable parenteral suspensions for treating inflammation in mammals, both humans and animals, using 1-(p-chlorobenzoyl)-2-methyl-5-methoxy-3-indolyl acetic acid, can be prepared by employing certain flocculating agents and deflocculating or suspending agents together, and by employing certain critical ratios of the various proportional amounts of medicament, vehicle, flocculating agent and deflocculating agent in the total suspension. Thus, the present invention relates to a composition of matter in the form of an improved parenteral suspension comprising from 10 to 200 mg/ml. of total suspension of the medicament, deflocculating agent as hereinafter defined, and flocculating agent as hereinafter defined, provided that the ratio of flocculating agent to deflocculating agent is from 45:1 to 300:1, especially 67:1 to 120:1, respectively, and the ratio of medicament to deflocculating agent is from 50:1 to 4000:1, especially 167:1 to 1000:1, respectively. In its preferred aspect, however, the parenteral suspension composition of the present invention will contain from 10 to 200 mg./ml. and especially 25 to 100 mg./ml. of total suspension of medicament; 0.05 to 0.20 mg./ml. and especially 0.10 to 0.15 mg./ml. of total suspension of deflocculating agent; and 5 to 15 mg./ml. and especially 10 to 12 mg./ml. of total suspension of flocculating agent. The parenteral suspension compositions of the present invention also contain certain excipients whose presence is desirable in preparing an acceptable parenteral suspension. The nature and proportional amounts of these excipients will be discussed in detail hereinafter.

The flocculating agents employed in preparing the parenteral suspension compositions of the present invention, while not regarded conventionally as flocculating agents, do, in fact, flocculate the medicament from the parenteral suspensions of the present invention. Flocculation is the aggregation of essentially monodispersed particles in a liquid into a light, fluffy agglomerate (floc) which separates from the liquid. The floc is formed and maintained primarily by weak Van der Waals forces. Flocculation is readily mediated by flocculating agents, which may be generally characterized by type as electrolytes, surfactants and polymers. While these types of flocculating agents produce flocculation by different mechanisms, the overall result is the same. The flocculating agents employed in the present invention are alkanols of 1 to 4 carbon atoms, and aromatic alcohols selected from the group consisting of benzyl alcohol, β-phenylethyl alcohol and cinnamyl alcohol, and mixtures of the above. Mixtures of varying proportions are suitable, and, for example, a mixture of benzyl alcohol and β-phenylethyl alcohol in a ratio of approximately 1:1 by weight has been found to give excellent results. As indicated previously, the flocculating agent will be employed in the parenteral suspension in amounts such that the ratio of flocculating agent to deflocculating agent is from 45:1 to 300:1, especially 67:1 to 120:1, respectively.

The deflocculating or suspending agents employed in the parenteral suspension compositions of the present invention are products derived from the condensation of polymers of ethylene oxide and containing from 10 to 50 oxyethylene repeating units, and esters of fat acids of 10 to 18 carbon atoms. Especially suitable are such condensation products from fat acid esters of sorbitol, particularly the lauric, stearic and oleic acid esters of sorbitol. The fat acid esters may be employed as mixtures from naturally occurring oils, which are esters of fat acids and glycerol. Thus, the deflocculating agent may be polyoxyethylene vegetable oil, available as Emulphor EL-719 from GAF Corporation. Naturally occurring fat acid mixtures may be employed to produce esters of sorbitol for condensation with polyoxyethylene. Thus, the deflocculating agent may be polyoxyethylene sorbitol lanolin, polyoxyethylene sorbitol tallow esters, and polyoxyethylene sorbitol tall oil, available, respectively, as Atlas G-1441, Atlas G-3284, and Atlox 1256 from Atlas Chemical Industries. Particularly preferred are esters of sorbitol and specific fat acids, especially lauric, stearic and oleic acids. Thus, the deflocculating agent may be polyoxyethylene sorbitan monolaurate, polyoxyethylene sorbitan monostearate, or polyoxyethylene sorbitan monooleate, available, respectively, as Atlas G-7596J, Tween 60 and Tween 80 from Atlas Chemical Industries. The last named product, Tween 80, which contains 20 oxyethylene units, has been found to be especially suitable. As indicated previously, the deflocculating agent will be employed in the parenteral suspension in amounts such that the ratio of medicament to deflocculating agent is from 50:1 to 4000:1, especially 167:1 to 1000:1, respectively.

By use of the particular flocculating and deflocculating agents described above, and in the critical range of proportionate amount ratios of the present invention, it is possible to obtain acceptable parenteral suspension compositions for 1-(p-chlorobenzoyl)-2-methyl-5-methoxy-3-indolyl acetic acid, which have the highly desirable properties of having the suspended material uniformly dispersed therein during the period of administration to the patient, while at the same time facilitating easy redispersion of that material after its flocculation and separation in the parenteral suspension composition. The problem thus avoided is that of caking, whereby the layer of material formed by flocculation and separation experiences a fusing together of the separate floc aggregates into larger masses until a consolidated, compact and near-monolithic formation is established. The result, of course, is an intractable hard cake which is highly resistant to redispersion.

In addition to the medicament, flocculating and deflocculating agents and water, conventional excipients and other materials are advantageously employed in preparing the parenteral suspension compositions of the present invention in accordance with good pharmaceutical practice. For example, the parenteral suspensions are sterile and preferably contain a bacteriological preservative to maintain sterility during use. Quarternary ammonium bacteriostats such as benzalkonium chloride may be used as well as phenyl mercuric acetate, phenyl mercuric nitrate, thimerosal, benzyl alcohol, or β-phenylethyl alcohol. These bacteriostats may suitably be used in a range of from 0.01 to 3.0 mg./ml. and preferably 0.1 to 0.2 mg./ml. of total suspension. An antioxidant may also be used to prevent oxidation of the medicament. Suitable anti-oxidants include sodium bisulfate, N-acetyl cysteine salts, sodium ascorbate, sodium meta bisulfite, sodium acetone bisulfite and other acceptable anti-oxidants known to the pharmaceutical art. These anti-oxidants may suitably be used in a range of 0.1 to 10.0 mg./ml. and preferably 0.2 to 3.5 mg./ml. In conjunction with the anti-oxidants, chelating agents such as disodium edetate may also be employed.

Viscosity inducing agents helpful in suspension characteristics of the composition, including cellulose derivatives such as hydroxymethyl cellulose, hudroxypropyl cellulose and methyl cellulose, may also be used in the formulation. For this purpose, one may use from 5.0 to 10.0 mg./ml. and preferably from 1.5 to 3.5 mg./ml. of such agents. Lecithin may also be used to provide helpful suspension characteristics for the parenteral suspension composition, being employed for this purpose in amounts of from 0.05 to 1.0 mg./ml. of total suspension, and preferably from 0.1 to 0.4 mg./ml. Finally, since the formulation is autoclaved to obtain initial sterility, an autoclaving aid such as sodium chloride is normally added to the formulation. The parenteral suspension compositions of the present invention are prepared by methods well known in the pharmaceutical art. For example, (1) there is first prepared a supersaturated NaCl aqueous solution such that the volume of water does not exceed 2½ times the amount of NaCl, and excess NaCl remains undissolved. (2) The medicament is then dispersed in the saline solution of (1) until a wet paste is formed. (3) The paste is sterilized by autoclaving at 121° C. under 15 p.s.i.g. pressure. (4) The viscosity inducing agent which is employed is then dispersed in water, clarified, and sterilized by autoclaving. (5) The other components of the total suspension composition are then added to water to form a solution. (6) The medicament paste from step (3) is then added aseptically to the viscosity inducing agent dispersion of step (4), and mixed. (7) The remaining suspension ingredients, prepared in step (5), are added aseptically to the mixture from step (6) by way of sterilizing membrane. (8) Sufficient water is added to the suspension from step (7) to give the total desired volume. (9) The suspension is then aseptically homogenized at 1500–2200 p.s.i.g., subdivided and distributed to suitable sterile containers.

DESCRIPTION OF SPECIFIC EMBODIMENTS

The following examples illustrate preparation of the improved parenteral suspension compositions of the present invention, and the improved characteristics thereof.

EXAMPLES 1-6

The following materials were admixed in a 1250 ml. bottle 25.75 g./l. of 1-(p-chlorobenzoyl)-2-methyl-5-methoxy-3-indolyl acetic acid, which was a sufficient amount of medicament to result in a concentration of 25 mg. per ml. in the final samples, allowing for an established 3.0% overage; 3.5 g./l. sodium bisulfite, 8.0 g./l. NaCl, and 780 ml. water (at 180° F.). The mixture (I) was autoclaved for 30 minutes at 121° C. under 15 p.s.i.g. Separately, 5.0 g./l. of sodium carboxymethylcellulose in 200 ml. of water (II) and g. of lecithin in 20 ml. of water (III) were autoclaved for 30 minutes at 121° C. Then, III was admixed with I for 2 hours, and the resultant mixture was poured into II. Another mixture (IV) was prepared from 9 g./l. of benzyl alcohol, 0.5 g./l. of disodium edetate, and water to give a final solution volume of 300 ml. Then, IV was added to the mixture of I, II, and III in sufficient quantity to give 900 ml. overall. A series of 90 ml. aliquots were then taken and homogenized using an homogenizer at 2000 p.s.i.g. and placed in 100 ml. q.s. graduated cylinder. Stock solutions were then prepared for polyoxyethylene (20) sorbitan monooleate by dissolving 7.5 g. of the material in 100 ml. of water, and of benzyl alcohol, using the alcohol per se. Varying quantities of the two stock solutions were then added to the mixture of I, II, III, and IV prepared as described above, to give six different samples, although it was necessary to add benzyl alcohol in only two samples, since the alcohol was already present in the desired amount in the other four samples. The samples were then brought to 100 ml., mixed for 2 to 3 hours, placed back in the cylinders and allowed to stand. Sedimentation volumes, ease of redispersion, and microscopic flocculation characteristics were assessed as determinative of required suspension properties. The quantities of flocculating agent and deflocculating agent employed and the results obtained are noted in the following table of values.

| Ex. No. | Polyoxyethylene (20) sorbitan monooleate (mg./ml.) | Benzyl alcohol (mg./ml.) | 24 Hour post mix and standing in cylinder | | |
|---|---|---|---|---|---|
| | | | Sediment Volume (%) | Redispersibility | Flocculation |
| 1 | 0.125 | 9 | 7 | Requires some shaking | Many small floccules |
| 2 | 0.250 | 9 | 4 | Caked, 98% redispersed with agitation | Fairly flocculated |
| 3 | 0.375 | 9 | 4 | Caked | — |
| 4 | 0.10 | 9 | 16.5 | Easily redispersed | Well flocculated |
| 5 | 0.10 | 10 | 17.5 | Easily redispersed | Very well flocculated |
| 6 | 0.10 | 12 | 20.5 | Easily redispersed | Very well flocculated |

As has been described hereinabove, in the improved parenteral suspension of the present invention, the flocculating and deflocculating components, in the concentrations and ratio of concentrations employed, exert a dramatic effect upon the suspension characteristics obtained, which can be well controlled despite the influence of other excipients. In this way, caking tendencies of the suspension are overcome, while at the same time over-flocculation of the suspension is prevented.

What is claimed is:

1. A parenteral suspension composition comprising 25 mg./ml. of total suspension of a medicament composition comprising 1-(p-chlorobenzoyl)-2-methyl-5-methoxy-3-indolyl acetic acid; 0.10 to 0.20 mg./ml. of total suspension of a deflocculating agent comprising polyoxyethylene (20) sorbitan monooleate; 9 to 12 mg./ml. of total suspension of a flocculating agent comprising benzyl alcohol; and water.

2. The composition of claim 1 wherein there is present a viscosity inducing agent, a preservative, an antioxidant, a chelating agent, and an autoclaving aid.

* * * * *